United States Patent [19]
Antoun

[11] Patent Number: 6,033,653
[45] Date of Patent: Mar. 7, 2000

[54] SHAMPOO PRODUCTS COMPRISING STARCH, A COMPOUND COMPRISING BORON, A COMPOUND COMPRISING ZINC, AND WATER

[76] Inventor: Jacques Antoun, 3630 General DeGaulle Dr., New Orleans, La. 70114

[21] Appl. No.: 08/844,707

[22] Filed: Apr. 18, 1997

Related U.S. Application Data

[63] Continuation-in-part of application No. PCT/US95/08847, Jun. 20, 1995, which is a continuation-in-part of application No. 08/262,953, Jun. 21, 1994, which is a continuation-in-part of application No. 07/863,795, Apr. 6, 1992, which is a continuation-in-part of application No. 07/609,392, Nov. 15, 1990, Pat. No. 5,102,916, which is a continuation-in-part of application No. 07/547,460, Jul. 3, 1990, abandoned.

[51] Int. Cl.$^7$ .............................. A61K 7/075; A61K 7/06
[52] U.S. Cl. ..................................... 424/70.19; 424/70.11; 424/70.1; 424/70.22; 424/70.8
[58] Field of Search .............................. 424/70.19, 70.11, 424/70.22, 401, 70.8

[56] References Cited

U.S. PATENT DOCUMENTS

| | | | |
|---|---|---|---|
| 124,751 | 3/1872 | Lauer | 424/642 |
| 143,133 | 8/1873 | Fehr | 424/642 |
| 415,208 | 11/1889 | Johnson | 424/642 X |
| 992,937 | 5/1911 | Brodbeck et al. | 424/642 X |
| 2,289,125 | 7/1942 | Keil | 424/642 X |
| 2,652,355 | 9/1953 | Ercoli et al. | 424/642 X |
| 4,643,939 | 2/1987 | Sugiymama et al. | 428/283 |
| 4,816,254 | 3/1989 | Moss | 424/642 |
| 4,908,355 | 3/1990 | Gettings et al. | 514/63 |
| 4,911,932 | 3/1990 | Clum et al. | 424/642 |
| 4,963,591 | 10/1990 | Fourman et al. | 514/944 |
| 5,015,470 | 5/1991 | Gibson | 424/70 |

FOREIGN PATENT DOCUMENTS 2653996 5/1991 France .

*Primary Examiner*—Sally Gardner-Lane
*Attorney, Agent, or Firm*—Garvey, Smith Nehrbass & Doody LLC

[57] ABSTRACT

A shampoo product is preferably made from boric acid, zinc oxide, starch, and other ingredients.

144 Claims, No Drawings

SHAMPOO PRODUCTS COMPRISING STARCH, A COMPOUND COMPRISING BORON, A COMPOUND COMPRISING ZINC, AND WATER

CROSS REFERENCE TO RELATED APPLICATIONS

This is a Continuation-inPart of International Patent Application PCT/US95/08847, filed Jun. 20, 1995, which is a Continuation-in-Part of U.S. patent application Ser. No. 08/262,953, filed Jun. 21, 1994, which is a Continuation-in-Part of U.S. patent application Ser. No. 07/863,795, filed Apr. 6, 1992, which is a Continuation-in-Part of U.S. patent application Ser. No. 07/609,392, filed Nov. 5, 1990, U.S. Pat. No. 5,102,916, which is a Continuation-in-Part of U.S. patent application Ser. No. 07/547,460, filed Jul. 3, 1990, abandoned, all of which (with their file histories) are hereby incorporated by reference.

SPECIFICATION

BACKGROUND OF THE INVENTION

1. Field of the Invention

The present invention relates to shampoo products.

2. General Background of the Invention

Hair loss occurs in many persons. Two relatively common causes of hair loss are male pattern baldness and alopecia areata. Alopecia areata is a disease affecting about two million people in the United States. It causes hair to fall out quickly, from scattered spots in the size a quarter to complete loss of all bodily hair, including the hair on the scalp. More information about alopecia areata can be obtained from the National Alopecia Areata Foundation (NAAF), P.O. Box 150760, San Rafael, Calif. 94915-0760, United States of America 1 (415) 456–4644, Fax: 1 (415) 456–4274. The NAAF publishes a bimonthly newsletter.

The inventor of the present invention is aware of a commercially available pharmaceutical composition for encouraging hair growth—Rogaine® with minoxidil, commercially available from the Upjohn Company. However, Rogaine® is relatively expensive and has been shown to cause hair regrowth in only about 63% of the women who have tried it (as opposed to 39% of women in a placebo group). According to an August 1991 newspaper article, only 39 percent of men using Rogaine® in clinical trials either grew new hair or stopped losing hair after six to eight months on the drug.

Upjohn advises that at least four months of treatment applying Rogaine twice a day are necessary before results can be seen with it. Further, newly grown hair is usually lost within a few months of stopping treatment with Rogaine.

Dr. Rudolf Japple has reportedly obtained U.S. and foreign patents on the use of the drug diphencyprone in the topical treatment of alopecia areata. The inventor is not aware of the effectiveness of this drug for the treatment of alopecia areata.

Thus, until now, there has been no effective relief for many persons suffering from hair loss due to male pattern baldness or alopecia areata.

Boric acid ($H_3BO_3$) is a mild antiseptic. It also has been used as a germicide. Borax is sodium tetraborate ($Na_2B_4O_7$) and is used as a laundry water softener. Its effect as a water softener is similar to that of ammonia.

Zinc ointment comprises zinc oxide and zinc stearate. Zinc ointment is used for treating various eruptions of the skin. Zinc stearate is an insoluble soap used as a dusting powder for infants. It has antiseptic properties but is irritating to mucous membranes. Zinc undecylenate is used in the treatment of athlete's foot.

U.S. Pat. No. 2,289,125 discloses a topical treatment for fungus infections of the skin in which, among other ingredients, boric acid, zinc oxide and corn starch are used. It is mentioned that the treatment can be mixed with water.

U.S. Pat. No. 2,652,355 describes a fungicidal topical composition in which cornstarch, zinc oxide and boric acid are primary ingredients.

U.S. Pat. No. 4,816,254 discloses an ointment in which boric acid, zinc oxide and gum powder are used to treat irritated skin.

U.S. Pat. No. 124,751 describes a zinc oxide composition to treat dandruff.

U.S. Pat. No. 992,937 discloses a composition in which boric acid, zinc oxide and talc are used to treat irritated skin.

U.S. Pat. No. 4,911,932 discloses a composition in which a composition containing, among other ingredients, borax, zinc oxide and water, is used to treat irritated skin.

None of the cited patents suggest a pharmaceutical composition consisting essentially of a compound comprising boron, a compound comprising zinc, starch, and water. Further, none of the patents suggest using a pharmaceutical composition containing a compound comprising boron, a compound comprising zinc, starch, and water to treat alopecia areata or male pattern baldness.

The following U.S. Patents are incorporated herein by reference: Re. U.S. Pat. Nos. 34,584, 4,345,080 and 4,379,753.

SUMMARY OF THE INVENTION

The present invention comprises a pharmaceutical composition which has been found to encourage hair growth in humans. The pharmaceutical composition of the present invention consists essentially of water, a compound comprising boron, a compound comprising zinc, and starch $((C_6H_{10}O_5)_x)$. The method of the present invention comprises applying a pharmaceutical composition containing a compound comprising boron, a compound comprising zinc, starch, and water to a person's scalp to treat alopecia areata or male pattern baldness.

Typically, when hair loss is limited to the scalp area, about 30 ml of the pharmaceutical composition is administered topically at least five times per week for three weeks, and is rinsed off approximately 20–30 minutes after being administered topically. More of the pharmaceutical composition is typically used if hair loss is not limited to the scalp area.

The pharmaceutical composition of the present invention can consist essentially of, by weight, 0.143%–3.93% starch, 1.00%–23.8% boron-containing compound, 0.625%–15.8% zinc-containing compound, and the balance water.

Preferably, in the pharmaceutical compound of the present invention and in the pharmaceutical compound used in the method of the present invention, the compound comprising boron is boric acid and the compound comprising zinc is zinc oxide.

One can mix the pharmaceutical composition of the present invention with commercially available shampoo for normal hair to help maintain the work of the pharmaceutical composition between treatments. One can also specially tailor the pharmaceutical composition of the present invention for use with normal, non-medicated, non-concentrated shampoos to help treat dandruff, to help dry oily hair, and to help give body to fine hair.

DETAILED DESCRIPTION OF THE PREFERRED EMBODIMENT

The pharmaceutical composition of the present invention comprises a zinc-containing compound and a boron-containing compound in a carrier suitable for topical application. Preferably, the zinc-containing compound is zinc oxide, the boron-containing compound is boric acid, and the carrier suitable for topical application is a mixture of starch and water.

The pharmaceutical composition of the present invention is preferably made from starch, zinc oxide, boric acid, and water.

It is believed that the present invention works because the zinc oxide cleans the skin, the boric acid kills germs, and the starch assists in penetration of the zinc oxide and boric acid into the pores of the skin. It is believed by the inventor that the starch stretches the skin to allow the zinc oxide and boric acid to get into the pores of the skin. The starch also acts as a carrier to hold the zinc oxide and boric acid in place on the scalp or other affected area.

It is believed that other zinc compounds may be substituted for zinc oxide, other boron compounds which provide boron ions can be substituted for boric acid, and another carrier could be substituted for starch and water.

The pharmaceutical composition of the present invention can consist essentially of, by weight, 0.143%–3.93% starch, 1.00%–23.8% boron-containing compound, 0.625%–15.8% zinc-containing compound, and the balance water (as in Table 1 when zinc oxide and boric acid are used). More preferably, the pharmaceutical composition of the present invention consists essentially of, by weight, 0.769%–2.73% starch, 5.22%–17.1% boron-containing compound, 3.31%–11.2% zinc-containing compound, and the balance water (as in Table 2 when zinc oxide and boric acid are used). Even more preferably, the pharmaceutical composition of the present invention consists essentially of, by weight, 1.48%–1.86% starch, 9.73%–12.1% boron-containing compound, 6.24%–7.82% zinc-containing compound, and the balance water (as in Table 3 when zinc oxide and boric acid are used).

The present invention also comprises a method of treating alopecia areata or male pattern baldness in a person in need of treatment comprising topically administering to the person in need of treatment a therapeutically effective amount of a pharmaceutical composition comprising water, starch, a compound comprising zinc, and a compound comprising boron.

The pharmaceutical composition used in the method of the present invention comprises 0.143%–3.93% by weight starch, 1.00%–23.8% by weight of the compound comprising boron, 625%–15.8% by weight of the compound comprising zinc, and water (as in Table 1 when zinc oxide and boric acid are used). More preferably, the pharmaceutical composition comprises 0.769%–2.73% by weight starch, 5.22%–17.1% by weight of the compound comprising boron, 3.31%–11.2% by weight of the compound comprising zinc, and water (as in Table 2 when zinc oxide and boric acid are used). Even more preferably, the pharmaceutical composition comprises 1.48%–1.86% by weight starch, 9.73%–12.1% by weight of the compound comprising boron, 6.24%–7.82% by weight of the compound comprising zinc, and water (as in Table 3 when zinc oxide and boric acid are used). Preferably, the compound comprising boron is boric acid, and the compound comprising zinc is zinc oxide.

TABLE 1

|  | Parts by wt. | % by wt. |
|---|---|---|
| Starch | 1–20 parts | 0.143%–3.93% |
| Boric acid | 6–120 parts | 1.00%–23.8% |
| Zinc oxide | 4–80 parts | .625%–15.8% |
| Water | 500 parts | 69.4%–97.8% |

TABLE 2

|  | Parts by wt. | % by wt. |
|---|---|---|
| Starch | 5–15 parts | .769%–2.73% |
| Boric acid | 30–90 parts | 5.22%–17.1% |
| Zinc oxide | 20–60 parts | 3.31%–11.2% |
| Water | 500 parts | 75.2%–90.1% |

TABLE 3

|  | Parts by wt. | % by wt. |
|---|---|---|
| Starch | 9–11 parts | 1.48%–1.86% |
| Boric acid | 54–66 parts | 9.73%–12.1% |
| Zinc oxide | 36–44 parts | 6.24%–7.82% |
| Water | 500 parts | 80.5%–83.5% |

To make the pharmaceutical composition of the present invention, the dry ingredients (starch, boron-containing compound, and zinc-containing compound) are mixed together, then the water is added. The mixture is boiled for an appropriate amount of time, stirring continuously.

Preferably, in the pharmaceutical composition of the present invention and in the pharmaceutical composition used in the method of the present invention, the boron-containing compound is boric acid and the zinc-containing compound is zinc oxide.

For example, the pharmaceutical composition of the present invention can comprise 10 parts by weight starch, 60 parts by weight boric acid, 40 parts by weight zinc oxide, and 500 parts by weight water. The dry ingredients (starch, boric acid, and zinc oxide) are mixed together, then the water is added. The mixture is boiled for about minutes, stirring continuously. The mixture will thicken, become smooth, and the final consistency may have minute lumps within the liquid. When a greater quantity of the dry ingredients is used, it may be desirable to boil the mixture for fewer than 20 minutes.

Preferably, before the pharmaceutical composition used in the method of the present invention is applied to the scalp of a subject in need of treatment, the bald spots are scrubbed with either pure lamb's wool or a soft-bristled brush made of animal hair. This cleanses residue from the skin; also, 100% wool is believed to help increase blood circulation. The pharmaceutical composition of the present invention is then rubbed on the bald spots and remains on the affected areas for 5–50 minutes, more preferably 10–40 minutes, even more preferably 20–30 minutes, and most preferably 25 minutes. The affected areas are then rinsed, removing any excess composition. If possible, this procedure is preferably repeated daily for 15 days. Thereafter, the procedure is preferably repeated 4 or 5 times per week for 2 or 3 months. Thereafter, the procedure is preferably repeated 1 or 2 times per week or per month.

The inventor has found that it usually takes three-fifteen days for pores to open and fifteen days to three months for fuzzy hair to appear. The inventor has found that it takes approximately one to six months for hair to grow to the point where it appears normal.

In the United States, four men suffering from alopecia areata have been treated, fourteen men and three women have been treated for male pattern baldness, and two women were treated for hair thinning. Fifteen persons in Lebanon and over ten persons in Spain have also been treated with the method of the present invention. All persons who were treated experienced new hair growth. Four specific examples follow from males treated in the United States. In each of these examples, the subjects were not concurrently treated with any other pharmaceutical composition or drug.

TABLE 4

| | Composition A | |
|---|---|---|
| | Parts by wt. | % by wt. |
| Starch | 10 parts | 1.64% |
| Boric acid | 60 parts | 9.84% |
| Zinc oxide | 40 parts | 6.56% |
| Water | 500 parts | 81.97% |
| Total | 610 parts | 100% |

EXAMPLE 1

A pharmaceutical composition (Composition A) was made by mixing 10 grams of Argo® pure starch with 60 grams of boric acid obtained from Crystal, Canning Road, Seffner, Fla., and 40 grams of zinc oxide obtained from Humco Laboratory, Texarkana, Tex. 75501, then adding 500 milliliters of water and boiling for 20 minutes, stirring continuously. The composition thickened and became smooth. The final consistency was a colloidal suspension in liquid.

D., a white male, lost about 80% of his hair at the age of 42 years. He also lost hair on his arms and legs. He was diagnosed by a dermatologist as having alopecia areata, and was treated by the dermatologist by being given Quaterzone ointment and injections of cortisone. The treatment lasted one year, but yielded no positive results.

D. was 44 years old at the time the treatment of the present invention began.

D. was treated with Composition A using the method of the present invention. Each treatment consisted of washing the hair and scalp, rinsing, then applying composition A and allowing it to remain on the affected area for about 25 minutes. Initially, he had a treatment six days per week for three weeks. Then, for two or three months, D. had 4 or 5 treatments per week. Thereafter, D. had about a treatment per week for about 15 months. At the age of 46 years, after approximately 220 treatments over 19 months, D. had nearly 100% hair regeneration.

EXAMPLE 2

At the age of 8, F., a white male, was diagnosed with alopecia areata by a medical doctor in the United States. Around the age of 16, F. had an onset of alopecia areata, lost patches of hair on his head and on other parts of his body. Until the age of 19, F. was treated with cortisone injections, Retin A 0.05%, Dithrocreme 0.025%, and Rogaine®, but with limited success. At the age of 20, F. was treated with Composition A, using the method of the present invention.

Initially, he had a treatment six days per week for two months. Then, for six months, F. had 2 or 3 treatments per week. Thereafter, F. had about 4 treatments per week for two or three months. Thereafter, he had a treatment every 3 weeks.

F. had approximately 400 treatments during a period of about three years.

Within eight weeks, F. began to experience regrowth of hair on his scalp and other affected areas. After thirty months, new hair completely covered the affected areas.

EXAMPLE 3

B., a white male, suffering from male pattern baldness, experienced severe thinning over approximately 50% of his scalp (top and rear). B. tried Dejojoba shampoo for six months, and Helsinkey shampoo for six months, but reported that the shampoos helped the hair grow very little.

B. was then treated with Composition A, using the method of the present invention 6 times a week for three weeks. Then, he was treated once per month for about 13 months. He had a total of about 45 treatments over 14 months.

Within three months, B. began to experience regrowth of hair on the affected area of his scalp. The new hair was initially fine, with thicker hair coming in after approximately seven months, the number of hairs per unit area in the affected areas increased to approximately 40–50% of the rest of the scalp, up from about 10%.

EXAMPLE 4

R., a white male, began losing hair in spots at the age of 26. He lost approximately 20% of the hair on his scalp. He also lost hair on his chin and arm. He was diagnosed by a dermatologist as having alopecia areata, and the dermatologist prescribed Quaterzone. He used Quaterzone for three weeks, without success. He also tried AG Pro, an over-the-counter product, for about a month, but with little improvement.

R. was treated using the method of the present invention, initially receiving 6 treatments per week for 3 weeks. Then, he received 2 treatments per week for 3 months. Thereafter, he received a treatment every 2 or 3 months. About twenty months after beginning treatment (about 40 treatments), R. again has a full head of hair, and the spots where he was missing hair elsewhere on his body have filled in with hair.

As evidenced by the examples presented herein, the pharmaceutical composition of the present invention, produced by the process of the present invention, when applied in accordance with the method of the present invention, can help in the treatment of alopecia areata and male pattern baldness.

Perhaps another suitable carrier could be substituted for starch in the pharmaceutical composition of the present invention.

One can mix the pharmaceutical composition of the present invention (such as Composition A) with commercially available shampoo for normal hair and use every day or every other day. In such a case, the pharmaceutical composition of the present invention preferably comprises 6% to 20% by volume of the mixture of shampoo and pharmaceutical composition. For example, most preferably one can mix 1 part by volume of the pharmaceutical composition of the present invention (such as Composition A) with 4 parts by volume of commercially available shampoo for normal hair and use every day or every other day. This shampoo of the present invention should be left on the scalp or other affected area for 5–10 minutes, then rinsed off. The shampoo of the present invention can help maintain the work of the pharmaceutical composition between treatments. The shampoo to mix with Composition A could comprise, for example, Quantun shampoo for normal hair, Terma Fuse shampoo for normal hair, or Zachi shampoo for normal hair. These shampoos can also be used with the mixtures whose descriptions follow.

Dandruff Treatment

When the pharmaceutical composition of the present invention is to be used to help treat dandruff, it can consist essentially of, by weight, 0.0014%–5.5% starch, 0.76%–15% boron-containing compound, 0.96%–19% zinc-containing compound, and the balance water (as in Table 5 when zinc oxide and boric acid are used). More preferably, the dandruff-treating pharmaceutical composition of the present invention consists essentially of, by weight, 0.75%–4.3% starch, 3.1%–12% boron-containing compound, 4.8%–15% zinc-containing compound, and the balance water (as in Table 6 when zinc oxide and boric acid are used). Even more preferably, the dandruff-treating pharmaceutical composition of the present invention consists essentially of, by weight, 1.6%–3.3% starch, 4.9%–9.6% boron-containing compound, 8.5%–11% zinc-containing compound, and the balance water (as in Table 7 when zinc oxide and boric acid are used). Most preferably, the dandruff-treating pharmaceutical composition of the present invention is Composition B.

The present invention also comprises a method of treating dandruff in a person in need of treatment comprising topically administering to the person in need of treatment a therapeutically effective amount of a pharmaceutical composition comprising water, starch, a compound comprising zinc, and a compound comprising boron, in a shampoo carrier.

The method of the present invention of treating dandruff comprises massaging into the dry scalp of a person a mixture of a pharmaceutical composition as in any of tables 5–8 (such as Composition B) and a shampoo carrier in a ratio of 1 part pharmaceutical composition to 0 to 30 parts shampoo. More preferably, the ratio is 1:1–1:8, even more preferably the ratio is 1:1–1:5, yet more preferably the ratio is 1:1–1:3, and most preferably the ratio is 1:2 (pharmaceutical composition:shampoo). The dandruff treating mixture of the present invention is massaged into the dry scalp of a person in need of treatment and allowed to remain for 5–40 minutes, more preferably 10–30 minutes, even more preferably 15–25 minutes, and most preferably 20 minutes. It is then rinsed out with water. Preferably, the compound comprising boron is boric acid, and the compound comprising zinc is zinc oxide.

TABLE 5

|  | Parts by wt. | % by wt. |
| --- | --- | --- |
| Starch | 1–30 parts | 0.0014%–5.5% |
| Boric acid | 5–90 parts | 0.76%–15% |
| Zinc oxide | 6–120 parts | .96%–19% |
| Water | 500 parts | 68%–98% |

TABLE 6

|  | Parts by wt. | % by wt. |
| --- | --- | --- |
| Starch | 5–25 parts | 0.75%–4.3% |
| Boric acid | 20–70 parts | 3.1%–12% |

TABLE 6-continued

|  | Parts by wt. | % by wt. |
| --- | --- | --- |
| Zinc oxide | 30–90 parts | 4.8%–15% |
| Water | 500 parts | 73%–90% |

TABLE 7

|  | Parts by wt. | % by wt. |
| --- | --- | --- |
| Starch | 10–20 parts | 1.6%–3.3% |
| Boric acid | 30–60 parts | 4.9%–9.6% |
| Zinc oxide | 54–66 parts | 8.5%–11% |
| Water | 500 parts | 77%–84% |

TABLE 8

| | Composition B | |
| --- | --- | --- |
|  | Parts by wt. | % by wt. |
| Starch | 15 parts | 2.4% |
| Boric acid | 45 parts | 7.2% |
| Zinc oxide | 60 parts | 9.7% |
| Water | 500 parts | 81% |
| Total | 620 parts | 100% |

Treatment for Oily Hair

When the pharmaceutical composition of the present invention is to be used to help treat oily hair, it can consist essentially of, by weight, 0.64%–13% starch, 1.5%–10% boron-containing compound, 1.5%–10% zinc-containing compound, and the balance water (as in Table 9 when zinc oxide and boric acid are used). More preferably, the composition of the present invention for treating oily hair consists essentially of, by weight, 3.3%–10% starch, 2.4%–78% boron-containing compound, 2.4%–78% zinc-containing compound, and the balance water (as in Table 10 when zinc oxide and boric acid are used). Even more preferably, the pharmaceutical composition of the present invention for treating oily hair consists essentially of, by weight, 5.8%–75% starch, 3.3%–6.7% boron-containing compound, 3.3%–6.7% zinc-containing compound, and the balance water (as in Table 11 when zinc oxide and boric acid are used). Most preferably, the pharmaceutical composition of the present invention for treating oily hair is Composition C.

The present invention also comprises a method of treating oily hair in a person in need of treatment comprising topically administering to the person in need of treatment a therapeutically effective amount of a pharmaceutical composition comprising water, starch, a compound comprising zinc, and a compound comprising boron, in a shampoo carrier.

The method of the present invention of treating oily hair comprises massaging into the dry scalp of a person a mixture of a pharmaceutical composition as in any of tables 9–12 (such as Composition C) and a shampoo carrier in a ratio of 1 part pharmaceutical composition to 0 to 30 parts shampoo. More preferably, the ratio is 1:1–1:8, even more preferably the ratio is 1:1–1:5, yet more preferably the ratio is 1:1–1:3, and most preferably the ratio is 1:2 (pharmaceutical composition:shampoo). The mixture of the present invention for treating oily hair is massaged into the dry scalp of a person in need of treatment and allowed to remain for 5–40 minutes, more preferably 10–30 minutes, even more preferably 15–25 minutes, and most preferably 20 minutes. It is then rinsed out with water. Preferably, the compound comprising boron is boric acid, and the compound comprising zinc is zinc oxide.

TABLE 9

|  | Parts by wt. | % by wt. |
| --- | --- | --- |
| Starch | 4–80 parts | 0.64%–13% |
| Boric acid | 10–60 parts | 1.5%–10% |
| Zinc oxide | 10–60 parts | 1.5%–10% |
| Water | 500 parts | 71%–95% |

TABLE 10

|  | Parts by wt. | % by wt. |
| --- | --- | --- |
| Starch | 20–60 parts | 3.3%–10% |
| Boric acid | 15–45 parts | 2.4%–78% |
| Zinc oxide | 15–45 parts | 2.4%–78% |
| Water | 500 parts | 77%–91% |

TABLE 11

|  | Parts by wt. | % by wt. |
| --- | --- | --- |
| Starch | 36–44 parts | 5.8%–75% |
| Boric acid | 20–40 parts | 3.3%–6.7% |
| Zinc oxide | 20–40 parts | 3.3%–6.7% |
| Water | 500 parts | 80%–87% |

TABLE 12

| Composition C | | |
| --- | --- | --- |
|  | Parts by wt. | % by wt. |
| Starch | 40 parts | 6.7% |
| Boric acid | 30 parts | 5.0% |
| Zinc oxide | 30 parts | 5.0% |
| Water | 500 parts | 83% |
| Total | 600 parts | 100% |

Treatment for Fine Hair

When the pharmaceutical composition of the present invention is to be used to help treat (add body to) fine hair, it can consist essentially of, by weight, 0.17%–10% starch, 1.6%–11% boron-containing compound, 0.80%–7.3% zinc-containing compound, and the balance water (as in Table 13 when zinc oxide and boric acid are used). More preferably, the composition of the present invention for treating fine hair consists essentially of, by weight, 0.85%–8.6% starch, 3.3%–8.8% boron-containing compound, 1.6%–5.4% zinc-containing compound, and the balance water (as in Table 14 when zinc oxide and boric acid are used). Even more preferably, the pharmaceutical composition of the present invention for treating fine hair consists essentially of, by weight, 1.7%–6.8% starch, 5.0%–7.1% boron-containing compound, 2.5%–4.4% zinc-containing compound, and the balance water (as in Table 15 when zinc oxide and boric acid are used). Most preferably, the pharmaceutical composition of the present invention for treating fine hair is Composition D.

The present invention also comprises a method of treating fine hair in a person in need of treatment comprising topically administering to the person in need of treatment a therapeutically effective amount of a pharmaceutical composition comprising water, starch, a compound comprising zinc, and a compound comprising boron, in a shampoo carrier.

The method of the present invention of treating fine hair comprises massaging into the dry scalp of a person a mixture of a pharmaceutical composition as in any of tables 13–16 (such as Composition D) and a shampoo carrier in a ratio of 1 part pharmaceutical composition to 0 to 30 parts shampoo. More preferably, the ratio is 1:1–1:8, even more preferably the ratio is 1:1–1:5, yet more preferably the ratio is 1:1–1:3, and most preferably the ratio is 1:2 (pharmaceutical composition: shampoo). The mixture of the present invention for treating fine hair is massaged into the dry scalp of a person in need of treatment and allowed to remain for 5–40 minutes, more preferably 10–30 minutes, even more preferably 15–25 minutes, and most preferably 20 minutes. It is then rinsed out with water. Preferably, the compound comprising boron is boric acid, and the compound comprising zinc is zinc oxide.

TABLE 13

|  | Parts by wt. | % by wt. |
| --- | --- | --- |
| Starch | 1–60 parts | 0.17%–10% |
| Boric acid | 10–60 parts | 1.6%–11% |
| Zinc oxide | 5–40 parts | 0.80%–7.3% |
| Water | 500 parts | 76%–97% |

TABLE 14

|  | Parts by wt. | % by wt. |
| --- | --- | --- |
| Starch | 5–50 parts | 0.85%–8.6% |
| Boric acid | 20–50 parts | 3.3%–8.8% |
| Zinc oxide | 10–30 parts | 1.6%–5.4% |
| Water | 500 parts | 79%–93% |

TABLE 15

|  | Parts by wt. | % by wt. |
| --- | --- | --- |
| Starch | 10–40 parts | 1.7%–6.8% |
| Boric acid | 30–40 parts | 5.0%–7.1% |
| Zinc oxide | 15–25 parts | 2.5%–4.4% |
| Water | 500 parts | 83%–90% |

TABLE 16

| Composition D | | |
| --- | --- | --- |
|  | Parts by wt. | % by wt. |
| Starch | 30 parts | 5.1% |
| Boric acid | 35 parts | 6.0% |
| Zinc oxide | 20 parts | 3.4% |
| Water | 500 parts | 85% |
| Total | 585 parts | 100% |

Alternative Treatment for Maintenance

Instead of using the pharmaceutical composition of Tables 1–4 mixed with shampoo for maintenance between treatments for alopecia areata or male pattern baldness, one could use the pharmaceutical composition of Tables 17–20 mixed with shampoo for maintenance between treatments for alopecia areata or male pattern baldness. In such a case, the pharmaceutical composition can consist essentially of, by weight, 0.74%–7.2% starch, 0.97%–16% boron-containing compound, 0.93%–13% zinc-containing compound, and the balance water (as in Table 17 when zinc oxide and boric acid are used). More preferably, the composition consists essentially of, by weight, 1.5%–5.3% starch, 4.1%–15% boron-containing compound, 1.6%–10% zinc-containing compound, and the balance water (as in Table 18 when zinc oxide and boric acid are used). Even more preferably, the pharmaceutical composition consists essentially of, by weight, 2.4%–4.3% starch, 5.8%–12% boron-containing compound, 2.5%–7.6% zinc-containing compound, and the balance water (as in Table 19 when zinc oxide and boric acid are used). Most preferably, the pharmaceutical composition is Composition E.

The present invention also comprises a method of maintenance in a person in need of treatment comprising topically administering to the person in need of treatment a therapeutically effective amount of a pharmaceutical composition comprising water, starch, a compound comprising zinc, and a compound comprising boron, in a shampoo carrier.

The method of the present invention of maintenance hair comprises massaging into the dry scalp of a person a mixture of a pharmaceutical composition as in any of tables 17–20 (such as Composition E) and a shampoo carrier in a ratio of 1 part pharmaceutical composition to 0 to 30 parts shampoo. More preferably, the ratio is 1:1–1:8, even more preferably the ratio is 1:1–1:5, yet more preferably the ratio is 1:1–1:3, and most preferably the ratio is 1:2 (pharmaceutical composition:shampoo). The mixture of the present invention for treating fine hair is massaged into the dry scalp of a person in need of treatment and allowed to remain for 5–40 minutes, more preferably 10–30 minutes, even more preferably 15–25 minutes, and most preferably 20 minutes. It is then rinsed out with water. Preferably, the compound comprising boron is boric acid, and the compound comprising zinc is zinc oxide.

TABLE 17

|  | Parts by wt. | % by wt. |
| --- | --- | --- |
| Starch: | 5–40 parts | 0.74%–7.2% |
| Boric acid: | 6–100 parts | 0.97%–16% |
| Zinc oxide: | 6–75 parts | 0.93%–13% |
| Water: | 500 parts | 70%–97% |

TABLE 18

|  | Parts by wt. | % by wt. |
| --- | --- | --- |
| Starch: | 10–30 parts | 1.5%–5.3% |
| Boric acid: | 25–95 parts | 4.1%–15% |
| Zinc oxide: | 10–60 parts | 1.6%–10% |
| Water: | 500 parts | 73%–92% |

TABLE 19

|  | Parts by wt. | % by wt. |
| --- | --- | --- |
| Starch: | 15–25 parts | 2.4%–4.3% |
| Boric acid: | 35–70 parts | 5.8%–12% |
| Zinc oxide: | 15–45 parts | 2.5%–7.6% |
| Water: | 500 parts | 78%–88% |

TABLE 20

| Composition E | Parts by wt. | % by wt. |
| --- | --- | --- |
| Starch: | 20 parts | 3.4% |
| Boric acid: | 50 parts | 8.4% |
| Zinc oxide: | 25 parts | 4.2% |
| Water: | 500 parts | 84% |
| Total: | 595 parts | 100% |

In the methods involving the pharmaceutical compositions of Tables 5–20, the treatment is preferably performed each time one shampoos.

In tables 21–31, all percentages are by weight. Also, water is added to each table in an amount to make up 100%.

TABLE 21

PRE-SHAMPOO FOR OILY HAIR

| Ingredients | Preferred Range | More Preferred Range | Most Preferred Range | Preferred Amount |
| --- | --- | --- | --- | --- |
| Zinc Oxide | .97%–19.4% | 4.85%–14.55% | 7.75%–12.125% | 9.7% |
| Boric Acid | .72%–14.4% | 3.6%–10.8% | 5.4%–9.0% | 7.2% |
| Corn Starch | .24%–4.8% | 1.2%–3.6% | 1.8%–3.0% | 2.4% |
| Tea Lauryl Sulfate | .01%–.2% | .05%–.15% | .075%–.125% | 0.1% |
| Sulfur | .006%–.12% | .03%–.09% | .045%–.075% | 0.06% |

TABLE 22

SHAMPOO FOR OILY HAIR

| Ingredients | Preferred Range | More Preferred Range | Most Preferred Range | Preferred Amount |
| --- | --- | --- | --- | --- |
| Zinc Oxide | .291%–5.82% | 1.455%–4.365% | 2.1825%–3.6375% | 2.91% |
| Boric Acid | .216%–4.32% | 1.08%–3.24% | 1.62%–2.7% | 2.16% |
| Tea Lauryl Sulfate | 1.403%–28.06% | 7.015%–21.045% | 10.5225%–17.5375% | 14.03% |
| Cocamide DEA | .175%–3.5% | .875%–2.625% | 1.3125%–2.1875% | 1.75% |
| Sodium Chloride | .175%–3.5% | .875%–2.625% | 1.3125%–2.1875% | 1.75% |
| Corn Starch | .072%–1.44% | .36%–1.08% | .54%–.90% | 0.72% |
| Lanolin | .014%–.28% | .07%–.21% | .105%–.175% | 0.14% |
| Aloe Barbadensis Gel | .014%–.28% | .07%–.21% | .105%–.175% | 0.14% |
| Methylchloro-isothihazolinone and Methyl-isotihazolinone | .07%–1.4% | .35%–1.05% | .525%–.875% | 0.7% |
| Menthol | .0105%–.21% | .0525%–.1575% | .07875%–.13125% | 0.105% |
| Fragrance | .0035%–.07% | .0175%–.0525% | .02625%–.04375% | 0.035% |
| Sulfur | .00018%–.0036% | .0009%–.0027% | .00135%–.00225% | 0.0018% |

TABLE 23

PRE-SHAMPOO FOR DANDRUFF

| Ingredients | Preferred Range | More Preferred Range | Most Preferred Range | Preferred Amount |
|---|---|---|---|---|
| Boric Acid | .84%–16.8% | 4.2%–12.6% | 6.3%–10.5% | 8.4% |
| Zinc Oxide | .42%–8.4% | 2.1%–6.3% | 3.15%–5.25% | 4.2% |
| Corn Starch | .34%–6.8% | 1.7%–5.1% | 2.55%–4.25% | 3.4% |
| Tea Lauryl Sulfate | .01%–.2% | .05%–.15% | .075%–.125% | 0.1% |
| Thiamine | .0001%–.002% | .0005%–.0015% | .00075%–.00125% | 0.001% |
| Riboflavin | .0001%–.002% | .0005%–.0015% | .00075%–.00125% | 0.001% |

TABLE 24

SHAMPOO FOR DANDRUFF

| Ingredients | Preferred Range | More Preferred Range | Most Preferred Range | Preferred Amount |
|---|---|---|---|---|
| Boric Acid | .252%–5.04% | 1.26%–3.78% | 1.89%–3.15% | 2.52% |
| Zinc Oxide | .126%–2.52% | .63%–1.89% | .945%–1.575% | 1.26% |
| Tea Lauryl Sulfate | 1.403%–28.06% | 7.015%–21.045% | 10.5225%–17.5375% | 14.03% |
| Cocamide DEA | .175%–3.5% | .875%–2.625% | 1.3125%–2.1875% | 1.75% |
| Sodium Chloride | .175%–3.5% | .875%–2.625% | 1.3125%–2.1875% | 1.75% |
| Corn Starch | .102%–2.04% | .51%–1.53% | .765%–1.275% | 1.02% |
| Lanolin | .014%–.28% | .07%–.21% | .105%–.175% | 0.14% |
| Aloe Barbadensis Gel | .014%–.28% | .07%–.21% | .105%–.175% | 0.14% |
| Methylchloroisotihazolinone and Methyl-isotihazolinone | .007%–.14% | .035%–105% | .0525%–.0875% | 0.07% |
| Menthol | .0105%–.21% | .0525%–.1575% | .07875%–.13125% | 0.105% |
| Fragrance | .0035%–.07% | .0175%–.0525% | .02625%–.04375% | 0.035% |
| Thiamine | .00003%–.0006% | .00015%–.00045% | .000225%–.000375% | 0.0003% |
| Riboflavin | .00003%–.0006% | .00015%–.00045% | .000225%–.000375% | 0.0003% |

TABLE 25

PRE-SHAMPOO FOR THINNING HAIR
(For people who are experiencing hair loss.)

| Ingredients | Preferred Range | More Preferred Range | Most Preferred Range | Preferred Amount |
|---|---|---|---|---|
| Boric Acid | .984%–19.68% | 4.92%–14.76% | 7.38%–12.3% | 9.84% |
| Zinc Oxide | .656%–13.12% | 3.28%–9.48% | 4.92%–8.2% | 6.56% |
| Corn Starch | .194%–3.88% | .97%–2.91% | 1.455%–2.425% | 1.94% |
| Tea Lauryl Sulfate | .01%–.2% | .05%–.15% | .075%–.125% | 0.1% |
| Thiamine | .000066%–.00132% | .00033%–.00099% | .000496%–.000825% | 0.00066% |
| Riboflavin | .000066%–.00132% | .00033%–.00099% | .000495%–.000825% | 0.00066% |
| Sulfur | .000048%–.00096% | .00024%–.00072% | .00036%–.0006% | 0.00048% |
| Retinol | .0000132%–.000264% | .000066%–.000198% | .000099%–.000165% | 0.000132% |
| Magnesium Gluconate | .0000026%–.000052% | .000013%–.000039% | .0000195%–.0000325% | 0.0000026% |
| Manganese Gluconate | .0000026%–.000052% | .000013 0–.000039% | .0000195%–.0000325% | 0.0000026% |

TABLE 26

SHAMPOO FOR THINNING HAIR
(For people who are experiencing hair loss.)

| Ingredients | Preferred Range | More Preferred Range | Most Preferred Range | Preferred Amount |
|---|---|---|---|---|
| Boric Acid | .2952%–5.904% | 1.476%–4.425% | 2.214%–3.69% | 2.952% |
| Zinc Oxide | .1968%–3.936% | .984%–2.952% | 1.476%–2.46% | 1.968% |
| Tea Lauryl Sulfate | 1.403%–28.06% | 7.015%–21.045% | 10.5225%–17.5375% | 14.03% |
| Cocamide DEA | .175%–3.5% | .875%–2.625% | 1.3125%–2.1875% | 1.75% |
| Sodium Chloride | .175%–3.5% | .875%–2.625% | 1.3125%–2.1875% | 1.75% |
| Corn Starch | .0582%–1.164% | .291%–.873% | .4365%–.7275% | 0.582% |
| Lanolin | .14%–.28% | .07%–.21% | .105%–.175% | 0.14% |
| Aloe Barbadensis Gel | .014%–.28% | .07%–.21% | .105%–.175% | 0.14% |
| Menthol | .0105%–.21% | .05255–.1575% | .07875%–.13125% | 0.105% |
| Methyl-chloro-isotihazolinone and Methyl-isotihazolinone | .007%–.14% | .035%–.105% | .0525%–.0875% | 0.07% |
| Fragrance | .0035%–.07% | .0175%–.0525% | .02625%–.04375% | 0.035% |
| Thiamine | .0000198%–.000396% | .000099%–.000297% | .0001485%–.0002475% | 0.000198% |
| Riboflavin | .0000198%–.000396% | .000099%–.000297% | .0001485%–.0002475% | 0.000198% |
| Sulfur | .0000144%–.000288% | .000072%–.000216% | .000108%–.00018% | 0.000144% |
| Retinol | .00000369%–.0000738% | .0000184%–.0000553% | .0000276%–.0000461% | 0.0000369% |
| Magnesium Gluconate | .00000078%–.0000156% | .0000039%–.0000117% | .0000058%–.00000097% | 0.0000078% |
| Manganese Gluconate | .00000078%–.0000156% | .0000039%–.0000117% | .0000058%–.0000097% | 0.0000078% |

TABLE 27

PRE-SHAMPOO FOR FINE HAIR

| Ingredients | Preferred Range | More Preferred Range | Most Preferred Range | Preferred Amount |
|---|---|---|---|---|
| Boric Acid | .5%–10.0% | 2.5%–7.5% | 3.75%–6.25% | 5.0% |
| ZincOxide | *5%–10.0% | 2.5%–2.7% | 3.75%–6.25% | 5.0% |
| Corn Starch | .61%–12.2% | 3.05%–9.15% | 3.05%–7.625% | 6.1% |
| Tea Lauryl Sulfate | .01%–.2% | .05%–.15% | .075%–.125% | 0.1% |
| Thiamine | .0001%–.002% | .00005%–.0015% | .00075%–.00125% | 0.001% |
| Riboflavin | .0001%–.002% | .00005%–.0015% | .00075%–.00125% | 0.001% |

TABLE 28

SHAMPOO FOR FINE HAIR

| Ingredients | Preferred Range | More Preferred Range | Most Preferred Range | Preferred Amount |
|---|---|---|---|---|
| Boric Acid | .15%–3.0% | .75%–2.25% | 1.125%–1.875% | 1.5% |
| Zinc Oxide | .15%–3.0% | .75%–2.25% | 1.125%–1.875% | 1.5% |
| Tea Lauryl Sulfate | 1.403%–28.06% | 7.015%–21.045% | 10.5225%–17.5375% | 14.03% |
| Corn Starch | .183–3.66% | .915%–2.745% | 1.3725%–2.2875% | 1.83% |
| Cocamide DEA | .175%–3.5% | .875%–2.625% | 1.3125%–2.1875% | 1.75% |
| Sodium Chloride | .175%–3.5% | .875%–2.625% | 1.3125%–2.1875% | 1.75% |
| Lanolin | .014%–.28% | .07%–.21% | .105%–.175% | 0.14% |
| Aloe Barbadensis Gel | .014%–.28% | .07%–.21% | .105%–.175% | 0.14% |
| Avena Sativa Extract | .014%–.28% | .07%–.21% | .105%–.175% | 0.14% |
| Menthol | .0105%–.21% | .0525%–.1575% | .07875%–.13125% | 0.105% |
| Methylchloro-isotihazolinone and Methyl-isotihazolinone | .007%–.14% | .035%–.105% | .0525%–.0875% | 0.07% |
| Thiamine | .000003%–.00006% | .000015%–.000045% | .0000225%–.0000375% | 0.00003% |
| Riboflavin | .000003%–.00006% | .000015%–.000045% | .0000225%–.0000375% | 0.00003% |

The active ingredients in the present composition of Tables 21–28 are natural components effective to the scalp and hair and extremely beneficial as a regulator and stabilizer to its capillary-dermis ecosystem.

The fundamental composition of the present invention disclosed in Tables 21–28 consists of vegetable oils, proteins and carbohydrates. They convey elasticity and softness to the hair aiding in the "compression" of the epidermis which conveys an exceptional shine. The conveyance of minerals, iron, magnesium, phosphorous, and most important sulphur molecules, cause an increase to the hair's thickness, creating an image of hair volume.

In addition, the conveyance of vitamins A, K, $B_1$, $B_2$ and PP guarantee regulation in the function of the hair cycle.

The ability to achieve the effects of nature is the answer to a natural balance within each individual's characteristics and tendencies.

Instructions for Application
(Pre-Shampoo) Active Ingredient No. 1
Preparation and Balance of the Scalp's Function With the client seated in the technician's chair, begin the application of the product throughout the scalp by sectioning parallel partitions of one centimeter (aided by a brush, hair-spatula, or applicator bottle). Once the application is finished, massage thoroughly following steps one to five:

Step #1, Relaxation
  Placing the palms of the hands against both temples and applying pressure with an upward rotating motion.

Step #2, Activation
  Placing the middle fingers against the collar bone, apply pressure with the thumb and with a rotating motion massage up and forward through the scalp area to the forehead.

Step #3, Softening
  Using the tips of the fingers and with both hands apply a massage, using little friction, through the entire scalp area.

Step #4, Filtration
  Using a soft motion with both hands, gently massage in a reverse motion from the forehead back to the neck area. Then allow the product to set for 15 minutes. DO NOT apply steam or heat.

Step #5, Shampoo
  Rinse gently (DO NOT CLEANSE). Then apply the ACTIVE INGREDIENT NO. 2 SPECIFIC SHAMPOO over the scalp and hair. Observe how the ACTIVE INGREDIENT NO. 2 forms a homogeneous mixture with the ACTIVE INGREDIENT NO. 1. Then moisten by adding small amounts of warm water until the scalp and hair are "relaxed"; comb gently untangling the hair and rinse thoroughly.

Proceed With Hair Styling

Hair treated with the compositions of the present invention does not require follow-up conditioning, except in cases which professional criteria favors and recommends the use of a specific product.

The compositions of the present invention shown in the right-most column of Tables 21–28 are manufactured in Spain by the HITRONIC S.L., (Laboratories) and distributed by HAIR-DRESSING TECHNOLOGY S.L., located in Camino de los Molonos, S/N, Zaragoza, Spain.

Oily Hair
(Pre-shampoo) Active Ingredient No. 1 (Table 21)

Recommended for treatment and care of the scalp and oily hair. This formulation is based on natural extracts of proteins and carbohydrates, with astringent effects; it also embodies a sulphur molecule insuring the function of the sebaceous secretion function.

Directions: Apply ACTIVE INGREDIENT NO. 1 with an applicator or hair-spatula over the entire scalp. Massage for 3 to 5 minutes. Allow to work for 10 to 15 minutes. Then apply ACTIVE INGREDIENT NO. 2.

(Shampoo) Active Ingredient No. 2 (Table 22)

This shampoo must be used exclusively in combination with the ACTIVE INGREDIENT NO. 1 which embodies phauriletosulphur (fauriletorsulphur) of trictulonamina (trietulonamina) tensionactive-non-irritant materials plus oligoelements and vitamins $B_1$, $B_2$ and PP.

Direction: Do not rinse. Apply ACTIVE INGREDIENT NO. 2 directly over the scalp and hair. Moisten with drops of warm water until foam develops. Comb and message for 3 to 4 minutes, then rinse.

Dandruff
(Pre-shampoo) Active Ingredient No. 1 (Table 23)

Recommended for the treatment of pitiriasis (Pityiases) simplescapitis (dry dandruff). This formulation is based on proteins, oligoelements and vitamins $B_1$, $B_2$ and PP group, acting as regulators for the Mitosis of the skin.

Directions: Apply over the scalp paying attention to the affected areas. Apply an activation strong massage. Allow to remain for 10 to 15 minutes. Then apply ACTIVE INGREDIENT NO. 2 (SPECIFIC SHAMPOO).
(Shampoo) Active Ingredient No. 2 (Table 24)

Based on natural elements acting favorably to the regulation of the cellular mitosis process.

Directions: Do not rinse. Apply directly over the scalp and hair. Moisten with drops of warm water until foam develops. Comb and massage for 3 to 5 minutes, then rinse.

Hair Loss Control (Pre-shampoo) Active Ingredient No. 1 (Table 25)

The natural ingredients function as regulators to the capillary cycles, altered by ethological reasons, stress, hormonal factors, sebacic excess, etc. Combining proteins of nourishing elements as well as minerals, sulphur and vitamins A, B and $B_1$.

Directions: Shake the product well. Proceed to apply thoroughly to the scalp. Massage to increase the blood flow. Relax the scalp to ultimately ease reverse circulation. Allow to rest for 15 to 20 minutes. Then apply ACTIVE INGREDIENT NO. 2 (SPECIFIC SHAMPOO).
(Shampoo) Active Ingredient No. 2 (Table 26)

Based on oat sprouts and with non-irritating phariletosulphur (fauriletersulphur), tenictulomamina (triettanolamino), tensionactive materials, it eases washing, protecting the compound's capillary lipids.

Directions: Do not rinse. Apply ACTIVE INGREDIENT NO. 2 directly over the scalp and hair. Moisten with drops of warm water until foam develops. Comb hair. After 5 minutes, apply a quick massage to take advantage of the active elements, then rinse.

Fine/Limp Hair (Pre-shampoo) Active Ingredient No. 1 (Table 27)

Natural and healthy treatment to restore and increase vitality to thin, limp hair.

Its composition consists of natural oat extracts, proteins, carbohydrates, cellulose, minerals and vitamins acting in such a method that hair increases volume creating great vitality and full body effect.

Directions: Apply to the scalp and hair and apply massage. Allow to rest for 10 to 15 minutes. Then apply ACTIVE INGREDIENT NO. 2 (SPECIFIC SHAMPOO).
(Shampoo) Active Ingredient No. 2 (Table 28)

Directions: Do not rinse. Apply ACTIVE INGREDIENT NO. 2 directly over the scalp and hair. Moisten with drops of warm water until foam develops. Allow to remain for 5 minutes, then rinse thoroughly.

TABLE 28

MULTIFUNCTIONAL NO STARCH POST-SHAMPOO

| Ingredients | Preferred Range | More Preferred Range | Most Preferred Range | Preferred Amount |
|---|---|---|---|---|
| Boric Acid | .26%–5.2% | 1.3%–3.9% | 1.95%–3.25% | 2.6% |
| Zinc Oxide | .24%–4.8% | 1.2%–3.6% | 1.8%–3.0% | 2.4% |
| Poliquaternium-11 | .20%–4.0% | 1.0%–3.0% | 1.5%–2.5% | 2.0% |
| Collagen | .05%–1.0% | .25%–.75% | .375%–.625% | 0.5% |
| Dimethicone | .025%– | .125%– | .1875%– | 0.25% |

TABLE 28-continued

MULTIFUNCTIONAL NO STARCH POST-SHAMPOO

| Ingredients | Preferred Range | More Preferred Range | Most Preferred Range | Preferred Amount |
|---|---|---|---|---|
| Copolyol | .50% | .375% | .3125% | |
| Lanolin | .01%–.20% | .05%–.15% | .075%–.125% | 0.1% |
| Citric Acid | .0025%–.05% | .0125%–.0375% | .01875%–.03125% | 0.025% |
| Alcohol | 2.5%–50.0% | 12.5%–37.5% | 18.75%–31.25% | 25.00% |

TABLE 28

MULTIFUNCTIONAL CONDITIONER

| Ingredients | Preferred Range | More Preferred Range | Most Preferred Range | Preferred Amount |
|---|---|---|---|---|
| Poliquaternium-11 | .7%–14.0% | 3.5%–10.5% | 5.25%–8.75% | 7.0% |
| Dimethicone Copolyol | .1%–2.0% | .5%–1.5% | .75%–1.25% | 1.0% |
| Zinc Oxide | .1%–2.0% | .5%–1.5% | .75%–1.25% | 1.0% |
| Boric Acid | .1%–2.0% | .5%–1.5% | .75%–1.25% | 1.0% |
| Collagen | .05%–1.0% | .25%–.75% | .375%–.625% | 0.5% |
| Lanolin | .01%–.2% | .05%–.15% | .075%–.125% | 0.1% |
| Methylchloro-isothiazolinone | .005%–.1% | .025%–.075% | .0375%–.0625% | 0.05% |
| Methylisothiazolinone | .005%–.1% | .025%–.075% | .0375%–.0625% | 0.05% |
| Citric Acid | .0025%–.05% | .0125%–.0375% | .01875%–.03125% | 0.025% |

TABLE 31

POST SHAMPOO FOR THINNING HAIR

| Ingredients | Preferred Range | More Preferred Range | Most Preferred Range | Preferred Amount |
|---|---|---|---|---|
| Alcohol | 2.5%–50.0% | 12.5%–37.5% | 18.75%–31.25% | 25.0% |
| Zinc Oxide | .27%–5.4% | 1.35%–4.05% | 2.025%–3.375% | 2.7% |
| Boric Acid | .23%–4.6% | 1.15%–3.45% | 1.725%–2.875% | 2.3% |
| Pathenol | .2%–4.0% | 1.0%–3.0% | 1.5%–2.5% | 2.0% |
| Hydrolyzed Serum Protein | .10%–4.0% | .50%–1.5% | .75%–1.25% | 1.0% |
| Yeast Extract | .10%–4.0% | .50%–1.5% | .75%–1.25% | 1.0% |
| Glucose | .10%–4.0% | .50%–1.5% | .75%–1.25% | 1.0% |
| Niacinamide | .10%–4.0% | .50%–1.5% | .75%–1.25% | 1.0% |
| Pyridoxine | .10%–4.0% | .50%–1.5% | .75%–1.25% | 1.0% |
| Hydrolized Glycosaminoglycans | .10%–4.0% | .50%–1.5% | .75%–1.25% | 1.0% |
| Biotin | .10%–4.0% | .50%–1.5% | .75%–1.25% | 1.0% |
| Fragrance | .03%–.60% | .15%–.45% | .225%–.375% | 0.3% |
| Polysorbate 20 | .01%–.20% | .05%–.15% | .075%–.125% | 0.1% |
| Arnica Montana Extract | .01%–.20% | .05%–.15% | .075%–.125% | 0.1% |
| Methylchloro-isothiazolinone | .005%–.10% | .025%–.075% | .0375%–.0625% | 0.05% |

TABLE 31-continued

POST SHAMPOO FOR THINNING HAIR

| Ingredients | Preferred Range | More Preferred Range | Most Preferred Range | Preferred Amount |
|---|---|---|---|---|
| Methylisothia-zolinone | .005%–.10% | .025%–.075% | .0375%–.0625% | 0.05% |

Multifunctional No Starch Post-Shampoo (Table 29)

Directions: Spread on the hair without previously wetting the hair, massaging the scalp. Do not rinse.

Post-Shampoo for Thinning Hair (Table 31)

Directions: Apply this product after the shampoo, drying the water excess with a towel. Massage gently for 3–5 minutes. Comb hair without rinsing.

The foregoing embodiments are presented by way of example only; the scope of the present invention is to be limited only by the following claims.

I claim:

1. A shampoo product comprising the following ingredients in the following amounts and water:
   0.291%–5.82% by weight Zinc Oxide, 0.216%–4.32% by weight Boric Acid, 1.403%–28.06% by weight Tea Lauryl Sulfate, 0.175%–3.5% by weight Cocamide DEA, 0.175%–3.5% by weight Sodium Chloride, 0.072%–1.44% by weight Corn Starch, 0.014%–0.28% by weight Lanolin, 0.014%–0.28% by weight Aloe Barbadensis Gel, 0.07%–1.4% by weight Methylchloroisotiha-zolinone and Methyl-isotihazolinone, 0.0105%–0.21% by weight Menthol, 0.0035%–0.07% by weight Fragrance, 0.00018%–0.0036% by weight Sulfur.

2. The shampoo product of claim 1, consisting essentially of said ingredients and water.

3. The shampoo product of claim 1, consisting of said ingredients and water.

4. The shampoo product of claim 1, wherein said ingredients are present in the following amounts:
   Zinc Oxide—1.455%–4.365%; Boric Acid—1.08%–3.24%; Tea Lauryl Sulfate—7.015%–21.045%; Cocamide DEA—0.875%–2.625%; Sodium Chloride—0.875%–2.625%; Corn Starch—0.36%–1.08%; Lanolin—0.07%–0.21%; Aloe Barbadensis Gel—0.07%–0.21%; Methylchloroisotiha-zolinone and Methyl-isotihazolinone—0.35%–1.05%; Menthol—0.0525%–0.1575%; Fragrance—0.0175%–0.0525%; Sulfur—0.0009%–0.0027%.

5. The shampoo product of claim 4, consisting essentially of said ingredients and water.

6. The shampoo product of claim 4, consisting of said ingredients and water.

7. The shampoo product of claim 1, wherein said ingredients are present in the following amounts:
   Zinc Oxide—2.1825%–3.6375%; Boric Acid—1.62%–2.7%; Tea Lauryl Sulfate—10.5225%–17.5375%; Cocamide DEA—1.3125%–2.1875%; Sodium Chloride—1.3125%–2.1875%; Corn Starch—0.54%–0.90%; Lanolin—0.105%–0.175%; Aloe Barbadensis Gel—0.105%–0.175%; Methylchloroisotiha-zolinone and Methyl-isotihazolinone—0.525%–0.875%; Menthol—0.07875%–0.13125%; Fragrance—0.02625%–0.04375%; Sulfur—0.00135%–0.00225%.

8. The shampoo product of claim 7, consisting essentially of said ingredients and water.

9. The shampoo product of claim 7, consisting of said ingredients and water.

10. A method of cleaning/maintaining hair comprising using the shampoo product of claim 1.

11. The method of claim 10, wherein the shampoo product consists essentially of said ingredients and water.

12. The method of claim 10, wherein the shampoo product consists of said ingredients and water.

13. The method of claim 10, wherein said ingredients are present in the following amounts:
   Zinc Oxide—1.455%–4.365%; Boric Acid—1.08%–3.24%; Tea Lauryl Sulfate—7.015%–21.045%; Cocamide DEA—0.875%–2.625%; Sodium Chloride—0.875%–2.625%; Corn Starch—0.36%–1.08%; Lanolin—0.07%–0.21%; Aloe Barbadensis Gel—0.07%–0.21%; Methylchloroisotiha-zolinone and Methyl-isotihazolinone—0.35%–1.05%; Menthol—0.0525%–0.1575%; Fragrance—0.0175%–0.0525%; Sulfur—0.0009%–0.0027%.

14. The method of claim 13, wherein the shampoo product consists essentially of said ingredients and water.

15. The method of claim 13, wherein the shampoo product consists of said ingredients and water.

16. The method of claim 10, wherein said ingredients are present in the following amounts:
   Zinc Oxide—2.1825%–3.6375%; Boric Acid—1.62%–2.7%; Tea Lauryl Sulfate—10.5225%–17.5375%; Cocamide DEA—1.3125%–2.1875%; Sodium Chloride—1.3125%–2.1875%; Corn Starch—0.54%–0.90%; Lanolin—0.105%–0.175%; Aloe Barbadensis Gel—0.105%–0.175%; Methylchloroisotiha-zolinone and Methyl-isotihazolinone—0.525%–0.875%; Menthol—0.07875%–0.13125%; Fragrance—0.02625%–0.04375%; Sulfur—0.00135%–0.00225%.

17. The method of claim 16, wherein the shampoo product consists essentially of said ingredients and water.

18. The method of claim 16, wherein the shampoo product consists of said ingredients and water.

19. A shampoo product comprising the following ingredients in the following amounts and water:
   0.252%–5.04% by weight Boric Acid; 0.126%–2.52% by weight Zinc Oxide; 1.403%–28.06% by weight Tea Lauryl Sulfate; 0.175%–3.5% by weight Cocamide DEA; 0.175%–3.5% by weight Sodium Chloride; 0.102%–2.04% by weight Corn Starch; 0.014%–0.28% by weight Lanolin; 0.014%–0.28% by weight Aloe Barbadensis Gel; 0.007%–0.14% by weight Methylchloroisotiha-zolinone and Methyl-isotihazolinone; 0.0105%–0.21% by weight Menthol; 0.0035%–0.07% by weight Fragrance; 0.00003%–0.0006% by weight Thiamine; 0.00003%–0.0006% by weight Riboflavin.

20. The shampoo product of claim 19, consisting essentially of said ingredients and water.

21. The shampoo product of claim 19, consisting of said ingredients and water.

22. The shampoo product of claim 19, wherein said ingredients are present in the following amounts:
   Boric Acid—1.26%–3.78%; Zinc Oxide—0.63%–1.89%; Tea Lauryl Sulfate—7.015%–21.045%; Cocamide DEA—0.875%–2.625%; Sodium Chloride—

0.875%–2.625%; Corn Starch—0.51%–1.53%; Lanolin—0.07%–0.21%; Aloe Barbadensis Gel—0.07%–0.21%; Methylchloroisotiha-zolinone and Methyl-isotihazolinone—0.035%–0.105%; Menthol—0.0525%–0.1575%; Fragrance—0.0175%–0.0525%; Thiamine—0.00015%–0.00045%; Riboflavin—0.00015%–0.00045%.

23. The shampoo product of claim 22, consisting essentially of said ingredients and water.

24. The shampoo product of claim 22, consisting of said ingredients and water.

25. The shampoo product of claim 19, wherein said ingredients are present in the following amounts:
Boric Acid—1.89%–3.15%; Zinc Oxide—0.945%–1.575%; Tea Lauryl Sulfate—10.5225%–17.5375%; Cocamide DEA—1.3125%–2.1875%; Sodium Chloride—1.3125%–2.1875% Corn Starch—0.765%–1.275%; Lanolin—0.105%–0.175%; Aloe Barbadensis Gel—0.105%–0.175% Methylchloroisotiha-zolinone and Methyl-isotihazolinone—0.0525%–0.0875%; Menthol—0.07875%–0.13125%; Fragrance—0.02625%–0.04375%; Thiamine—0.000225%–0.000375%; Riboflavin—0.000225%–0.000375%.

26. The shampoo product of claim 25, consisting essentially of said ingredients and water.

27. The shampoo product of claim 25, consisting of said ingredients and water.

28. A method of cleaning/maintaining hair comprising using the shampoo product of claim 19.

29. The method of claim 28, wherein the shampoo product consists essentially of said ingredients and water.

30. The method of claim 28, wherein the shampoo product consists of said ingredients and water.

31. The method of claim 28, wherein said ingredients are present in the following amounts:
Boric Acid—1.26%–3.78%; Zinc Oxide—0.63%–1.89%; Tea Lauryl Sulfate—7.015%–21.045%; Cocamide DEA—0.875%–2.625%; Sodium Chloride—0.875%–2.625%; Corn Starch—0.51%–1.53%; Lanolin—0.07%–0.21%; Aloe Barbadensis Gel—0.07%–0.21%; Methylchloroisotiha-zolinone and Methyl-isotihazolinone—0.035%–0.105%; Menthol—0.0525%–0.1575%; Fragrance—0.0175%–0.0525%; Thiamine—0.00015%–0.00045%; Riboflavin—0.00015%–0.00045%.

32. The method of claim 31, wherein the shampoo product consists essentially of said ingredients and water.

33. The method of claim 31, wherein the shampoo product consists of said ingredients and water.

34. The method of claim 28, wherein said ingredients are present in the following amounts:
Boric Acid—1.89%–3.15%; Zinc Oxide—0.945%–1.575%; Tea Lauryl Sulfate—10.5225%–17.5375%; Cocamide DEA—1.3125%–2.1875%; Sodium Chloride—1.3125%–2.1875% Corn Starch—0.765%–1.275%; Lanolin—0.105%–0.175%; Aloe Barbadensis Gel—0.105%–0.175% Methylchloroisotiha-zolinone and Methyl-isotihazolinone—0.0525%–0.0875%; Menthol—0.07875%–0.13125%; Fragrance—0.02625%–0.04375%; Thiamine—0.000225%–0.000375%; Riboflavin—0.000225%–0.000375%.

35. The method of claim 34, wherein the shampoo product consists essentially of said ingredients and water.

36. The method of claim 34, wherein the shampoo product consists of said ingredients and water.

37. A shampoo product comprising the following ingredients in the following amounts and water:
0.984%–19.68% by weight Boric Acid; 0.656%–13.12% by weight Zinc Oxide; 0.194%–3.88% by weight Corn Starch; 0.01%–0.2% by weight Tea Lauryl Sulfate; 0.000066%–0.00132% by weight Thiamine; 0.000066%–0.00132% by weight Riboflavin; 0.000048%–0.00096% by weight Sulfur 0.0000132%–0.000264% by weight Retinol; 0.0000026%–0.000052% by weight Magnesium Gluconate; 0.0000026%–0.000052% by weight Manganese Gluconate.

38. The shampoo product of claim 37, consisting essentially of said ingredients and water.

39. The shampoo product of claim 37, consisting of said ingredients and water.

40. The shampoo product of claim 37, wherein said ingredients are present in the following amounts:
Boric Acid—4.92%–14.76%; Zinc Oxide—3.28%–9.48%; Corn Starch—0.97%–2.91% Tea Lauryl Sulfate—0.05%–0.15%; Thiamine—0.00033%–0.00099%; Riboflavin—0.00033%–0.00099%; Sulfur—0.00024%–0.00072%; Retinol—0.000066%–0.000198%; Magnesium Gluconate—0.000013%–0.000039%; Manganese Gluconate—0.000013% 0.000039%.

41. The shampoo product of claim 40, consisting essentially of said ingredients and water.

42. The shampoo product of claim 40, consisting of said ingredients and water.

43. The shampoo product of claim 37, wherein said ingredients are present in the following amounts:
Boric Acid—7.38%–12.3%; Zinc Oxide—4.92%–8.2%; Corn Starch—1.455%–2.425%; Tea Lauryl Sulfate—0.075%–0.125%; Thiamine—0.000496%–0.000825%; Riboflavin—0.000495%–0.000825%; Sulfur—0.00036%–0.0006%; Retinol—0.000099%–0.000165%; Magnesium Gluconate—0.0000195%–0.0000325%; Manganese Gluconate 0.0000195%–0.0000325%.

44. The shampoo product of claim 43, consisting essentially of said ingredients and water.

45. The shampoo product of claim 43, consisting of said ingredients and water.

46. A method of cleaning/maintaining hair comprising using the shampoo product of claim 37.

47. The method of claim 46, wherein the shampoo product consists essentially of said ingredients and water.

48. The method of claim 46, wherein the shampoo product consists of said ingredients and water.

49. The method of claim 46, wherein said ingredients are present in the following amounts:
Boric Acid—4.92%–14.76%; Zinc Oxide—3.28%–9.48%; Corn Starch—0.97%–2.91% Tea Lauryl Sulfate—0.05%–0.15%; Thiamine—0.00033%–0.00099%; Riboflavin—0.00033%–0.00099%; Sulfur—0.00024%–0.00072%; Retinol—0.000066%–0.000198%; Magnesium Gluconate—0.000013%–0.000039%; Manganese Gluconate—0.000013% 0.000039%.

50. The method of claim 49, wherein the shampoo product consists essentially of said ingredients and water.

51. The method of claim 49, wherein the shampoo product consists of said ingredients and water.

52. The method of claim 46, wherein said ingredients are present in the following amounts:

Boric Acid—7.38%–12.3%; Zinc Oxide—4.92%–8.2%; Corn Starch—1.455%–2.425%; Tea Lauryl Sulfate—0.075%–0.125%; Thiamine—0.000496%–0.000825%; Riboflavin—0.000495%–0.000825%; Sulfur—0.00036%–0.0006%; Retinol—0.000099%–0.000165%; Magnesium Gluconate—0.0000195%–0.0000325%; Manganese Gluconate 0.0000195%–0.0000325%.

53. The method of claim 52, wherein the shampoo product consists essentially of said ingredients and water.

54. The method of claim 52, wherein the shampoo product consists of said ingredients and water.

55. A shampoo product comprising the following ingredients in the following amounts and water:
   0.2952%–5.904% by weight Boric Acid; 0.1968%–3.936% by weight Zinc Oxide; 1.403%–28.06% by weight Tea Lauryl Sulfate; 0.175%–3.5% by weight Cocamide DEA; 0.175%–3.5% by weight Sodium Chloride; 0.0582%–1.164% by weight Corn Starch; 0.14%–0.28% by weight Lanolin; 0.014%–0.28% by weight Aloe Barbadensis Gel; 0.0105%–0.21% by weight Menthol; 0.007%–0.14% by weight Methylchloroisotiha-zolinone and Methyl-isothazolinone; 0.0035%–0.07% by weight Fragrance; 0.0000198%–0.000396% by weight Thiamine; 0.0000198%–0.000396% by weight Riboflavin; 0.0000144%–0.000288% by weight Sulfur; 0.00000369%–0.0000738% by weight Retinol; 0.00000078%–0.0000156% by weight Magnesium Gluconate; 0.00000078%–0.0000156% by weight Manganese Gluconate.

56. The shampoo product of claim 55, consisting essentially of said ingredients and water.

57. The shampoo product of claim 55, consisting of said ingredients and water.

58. The shampoo product of claim 55, wherein said ingredients are present in the following amounts:
   Boric Acid—1.476%–4.425%; Zinc Oxide—0.984%–2.952%; Tea Lauryl Sulfate—7.015%–21.045%; Cocamide DEA—0.875%–2.625%; Sodium Chloride—0.875%–2.625%; Corn Starch—0.291%–0.873%; Lanolin—0.07%–0.21%; Aloe Barbadensis Gel—0.07%–0.21%; Menthol—0.05255–0.1575%; Methylchloroisotiha-zolinone and Methyl-isothazolinone—0.035%–0.105%; Fragrance—0.0175%–0.0525%; Thiamine—0.000099%–0.000297%; Riboflavin—0.000099%–0.000297%; Sulfur—0.000072%–0.000216%; Retinol—0.0000184%–0.0000553%; Magnesium Gluconate—0.0000039%–0.0000117%; Manganese Gluconate—0.0000039%–0.0000117%.

59. The shampoo product of claim 58, consisting essentially of said ingredients and water.

60. The shampoo product of claim 58, consisting of said ingredients and water.

61. The shampoo product of claim 55, wherein said ingredients are present in the following amounts:
   Boric Acid—2.214%–3.69%; Zinc Oxide—1.476%–2.46%; Tea Lauryl Sulfate—10.5225%–17.5375%; Cocamide DEA—1.3125%–2.1875%; Sodium Chloride—1.3125%–2.1875%; Corn Starch—0.4365%–0.7275%; Lanolin—0.105%–0.175%; Aloe Barbadensis Gel—0.105%–0.175%; Menthol—0.07875%–0.13125%; Methylchloroisotiha-zolinone and Methyl-isothazolinone—0.0525%–0.0875%; Fragrance—0.02625%–0.04375%; Thiamine—0.0001485%–0.0002475%; Riboflavin—0.0001485%–0.0002475%; Sulfur—0.000108%–0.00018%; Retinol—0.0000276%–0.0000461%; Magnesium Gluconate—0.0000058%–0.00000097%; Manganese Gluconate—0.0000058%–0.0000097%.

62. The shampoo product of claim 61, consisting essentially of said ingredients and water.

63. The shampoo product of claim 61, consisting of said ingredients and water.

64. A method of cleaning/maintaining hair comprising using the shampoo product of claim 55.

65. The method of claim 64, wherein the shampoo product consists essentially of said ingredients and water.

66. The method of claim 64, wherein the shampoo product consists of said ingredients and water.

67. The method of claim 64, wherein said ingredients are present in the following amounts:
   Boric Acid—1.476%–4.425%; Zinc Oxide—0.984%–2.952%; Tea Lauryl Sulfate—7.015%–21.045%; Cocamide DEA—0.875%–2.625%; Sodium Chloride—0.875%–2.625%; Corn Starch—0.291%–0.873%; Lanolin—0.07%–0.21%; Aloe Barbadensis Gel—0.07%–0.21%; Menthol—0.05255–0.1575%; Methylchloroisotiha-zolinone and Methyl-isothazolinone—0.035%–0.105%; Fragrance—0.0175%–0.0525%; Thiamine—0.000099%–0.000297%; Riboflavin—0.000099%–0.000297%; Sulfur—0.000072%–0.000216%; Retinol—0.0000184%–0.0000553%; Magnesium Gluconate—0.0000039%–0.0000117%; Manganese Gluconate—0.0000039%–0.0000117%.

68. The method of claim 67, wherein the shampoo product consists essentially of said ingredients and water.

69. The method of claim 67, wherein the shampoo product consists of said ingredients and water.

70. The method of claim 64, wherein said ingredients are present in the following amounts:
   Boric Acid—2.214%–3.69%; Zinc Oxide—1.476%–2.46%; Tea Lauryl Sulfate—10.5225%–17.5375%; Cocamide DEA—1.3125%–2.1875%; Sodium Chloride—1.3125%–2.1875%; Corn Starch—0.4365%–0.7275%; Lanolin—0.105%–0.175%; Aloe Barbadensis Gel—0.105%–0.175%; Menthol—0.07875%–0.13125%; Methylchloroisotiha-zolinone and Methyl-isothazolinone—0.0525%–0.0875%; Fragrance—0.02625%–0.04375%; Thiamine—0.0001485%–0.0002475%; Riboflavin—0.0001485%–0.0002475%; Sulfur—0.000108%–0.00018%; Retinol—0.0000276%–0.0000461%; Magnesium Gluconate—0.0000058%–0.00000097%; Manganese Gluconate—0.0000058%–0.0000097%.

71. The method of claim 70, wherein the shampoo product consists essentially of said ingredients and water.

72. The method of claim 70, wherein the shampoo product consists of said ingredients and water.

73. A shampoo product comprising the following ingredients in the following amounts and water:
   0.15%–3.0% by weight Boric Acid; 0.15%–3.0% by weight Zinc Oxide; 1.403%–28.06% by weight Tea Lauryl Sulfate; 0.183–3.66% by weight Corn Starch; 0.175%–3.5% by weight Cocamide DEA;

0.175%–3.5% by weight Sodium Chloride; 0.014%–0.28% by weight Lanolin; 0.014%–0.28% by weight Aloe Barbadensis Gel; 0.014%–0.28% by weight Avena Sativa Extract; 0.0105%–0.21% by weight Menthol; 0.007%–0.14% by weight Methylchloroisotiha-zolinone and Methyl-isotihazolinone; 0.000003%–0.00006% by weight Thiamine; 0.000003%–0.00006% by weight Riboflavin.

74. The shampoo product of claim 73, consisting essentially of said ingredients and water.

75. The shampoo product of claim 73, consisting of said ingredients and water.

76. The shampoo product of claim 73, wherein said ingredients are present in the following amounts:
Boric Acid—0.75%–2.25%; Zinc Oxide—0.75%–2.25%; Tea Lauryl Sulfate—7.015%–21.045%; Corn Starch—0.915%–2.745%; Cocamide DEA—0.875%–2.625%; Sodium Chloride—0.875%–2.625%; Lanolin—0.07%–0.21%; Aloe Barbadensis Gel—0.07%–0.21%; Avena Sativa Extract—0.07%–0.21%; Menthol—0.0525%–0.1575%; Methylchloroisotiha-zolinone and Methyl-isotihazolinone—0.035%–0.105%; Thiamine—0.000015%–0.000045%; Riboflavin—0.000015%–0.000045%.

77. The shampoo product of claim 76, consisting essentially of said ingredients and water.

78. The shampoo product of claim 76, consisting of said ingredients and water.

79. The shampoo product of claim 73, wherein said ingredients are present in the following amounts:
Boric Acid—1.125%–1.875%; Zinc Oxide—1.125%–1.875%; Tea Lauryl Sulfate—10.5225%–17.5375%; Corn Starch—1.3725%–2.2875%; Cocamide DEA—1.3125%–2.1875%; Sodium Chloride—1.3125%–2.1875%; Lanolin—0.105%–0.175%; Aloe Barbadensis Gel—0.105%–0.175%; Avena Sativa Extract—0.105%–0.175%; Menthol—0.07875%–0.13125%; Methylchloroisotiha-zolinone and Methyl-isotihazolinone—0.0525%–0.0875%; Thiamine—0.0000225%–0.0000375%; Riboflavin—0.0000225%–0.0000375%.

80. The shampoo product of claim 79, consisting essentially of said ingredients and water.

81. The shampoo product of claim 79, consisting of said ingredients and water.

82. A method of cleaning/maintaining hair comprising using the shampoo product of claim 73.

83. The method of claim 82, wherein the shampoo product consists essentially of said ingredients and water.

84. The method of claim 82, wherein the shampoo product consists of said ingredients and water.

85. The method of claim 82, wherein said ingredients are present in the following amounts:
Boric Acid—0.75%–2.25%; Zinc Oxide—0.75%–2.25%; Tea Lauryl Sulfate—7.015%–21.045%; Corn Starch—0.915%–2.745%; Cocamide DEA—0.875%–2.625%; Sodium Chloride—0.875%–2.625%; Lanolin—0.07%–0.21%; Aloe Barbadensis Gel—0.07%–0.21%; Avena Sativa Extract—0.07%–0.21%; Menthol—0.0525%–0.1575%; Methylchloroisotiha-zolinone and Methyl-isotihazolinone—0.035%–0.105%; Thiamine—0.000015%–0.000045%; Riboflavin—0.000015%–0.000045%.

86. The method of claim 85, wherein the shampoo product consists essentially of said ingredients and water.

87. The method of claim 85, wherein the shampoo product consists of said ingredients and water.

88. The method of claim 82, wherein said ingredients are present in the following amounts:
Boric Acid—1.125%–1.875%; Zinc Oxide—1.125%–1.875%; Tea Lauryl Sulfate—10.5225%–17.5375%; Corn Starch—1.3725%–2.2875%; Cocamide DEA—1.3125%–2.1875%; Sodium Chloride—1.3125%–2.1875%; Lanolin—0.105%–0.175%; Aloe Barbadensis Gel—0.105%–0.175%; Avena Sativa Extract—0.105%–0.175%; Menthol—0.07875%–0.13125%; Methylchloroisotiha-zolinone and Methyl-isotihazolinone—0.0525%–0.0875%; Thiamine—0.0000225%–0.0000375%; Riboflavin—0.0000225%–0.0000375%.

89. The method of claim 88, wherein the shampoo product consists essentially of said ingredients and water.

90. The method of claim 91, wherein the shampoo product consists of said ingredients and water.

91. A shampoo product comprising the following ingredients in the following amounts and water:
0.26%–5.2% by weight Boric Acid; 0.24%–4.8% by weight Zinc Oxide; 0.20%–4.0% by weight Poliquaternium-11; 0.05%–1.0% by weight Collagen; 0.025%–0.50% by weight Dimethicone Copolyol; 0.01%–0.20% by weight Lanolin; 0.0025%–0.05% by weight Citric Acid; 2.5%–50.0% by weight Alcohol.

92. The shampoo product of claim 91, consisting essentially of said ingredients and water.

93. The shampoo product of claim 91 consisting of said ingredients and water.

94. The shampoo product of claim 91, wherein said ingredients are present in the following amounts:
Boric Acid—1.3%–3.9%; Zinc Oxide—1.2%–3.6%; Poliquaternium-11—1.0%–3.0%; Collagen—0.25%–0.75%; Dimethicone Copolyol—0.125%–0.375%; Lanolin—0.05%–0.15%; Citric Acid—0.0125%–0.0375%; Alcohol—12.5%–37.5%.

95. The shampoo product of claim 94, consisting essentially of said ingredients and water.

96. The shampoo product of claim 94, consisting of said ingredients and water.

97. The shampoo product of claim 91, wherein said ingredients are present in the following amounts:
Boric Acid—1.95%–3.25%; Zinc Oxide—1.8%–3.0%; Poliquaternium-11—1.5%–2.5%; Collagen—0.375%–0.625%; Dimethicone Copolyol—0.1875%–0.3125%; Lanolin—0.075%–0.125%; Citric Acid—0.01875%–0.03125%; Alcohol—18.75%–31.25%.

98. The shampoo product of claim 97, consisting essentially of said ingredients and water.

99. The shampoo product of claim 97, consisting of said ingredients and water.

100. A method of cleaning/maintaining hair comprising using the shampoo product of claim 91.

101. The method of claim 100, wherein the shampoo product consists essentially of said ingredients and water.

102. The method of claim 100, wherein the shampoo product consists of said ingredients and water.

103. The method of claim 100, wherein said ingredients are present in the following amounts:
Boric Acid—1.3%–3.9%; Zinc Oxide—1.2%–3.6%; Poliquaternium-11—1.0%–3.0%; Collagen—0.25%–0.75%; Dimethicone Copolyol—

0.125%–0.375%; Lanolin—0.05%–0.15%; Citric Acid—0.0125%–0.0375%; Alcohol—12.5%–37.5%.

104. The method of claim 103, wherein the shampoo product consists essentially of said ingredients and water.

105. The method of claim 103, wherein the shampoo product consists of said ingredients and water.

106. The method of claim 100, wherein said ingredients are present in the following amounts:

Boric Acid—1.95%–3.25%; Zinc Oxide—1.8%–3.0%; Poliquaternium-11—1.5%–2.5%; Collagen—0.375%–0.625%; Dimethicone Copolyol—0.1875%–0.3125%; Lanolin—0.075%–0.125%; Citric Acid—0.01875%–0.03125%; Alcohol—18.75%–31.25%.

107. The method of claim 106, wherein the shampoo product consists essentially of said ingredients and water.

108. The method of claim 106, wherein the shampoo product consists of said ingredients and water.

109. A shampoo product comprising the following ingredients in the following amounts and water:

0.7%–14.0% by weight Poliquaternium-11; 0.1%–2.0% by weight Dimethicone Copolyol; 0.1%–2.0% by weight Zinc Oxide; 0.1%–2.0% by weight Boric Acid; 0.05%–1.0% by weight Collagen; 0.01%–0.2% by weight Lanolin; 0.005%–0.1% by weight Methylchloroisothia-zolinone; 0.005%–0.1% by weight Methylisothia-zolinone; 0.0025%–0.05% by weight Citric Acid.

110. The shampoo product of claim 109, consisting essentially of said ingredients and water.

111. The shampoo product of claim 109, consisting of said ingredients and water.

112. The shampoo product of claim 109, wherein said ingredients are present in the following amounts:

Poliquaternium-11—3.5%–10.5%; Dimethicone Copolyol—0.5%–1.5%; Zinc Oxide—0.5%–1.5%; Boric Acid-0.5%–0.5%; Collagen-0.25%–0.75%; Lanolin—0.05%–0.15%; Methylchloroisothia-zolinone—0.025%–0.075%; Methylisothia-zolinone—0.025%–0.075%; Citric Acid—0.0125%–0.0375%.

113. The shampoo product of claim 112, consisting essentially of said ingredients and water.

114. The shampoo product of claim 112, consisting of said ingredients and water.

115. The shampoo product of claim 109, wherein said ingredients are present in the following amounts:

Poliquaternium-11—5.25%–8.75%; Dimethicone Copolyol—0.75%–1.25%; Zinc Oxide—0.75%–1.25%; Boric Acid—0.75%–1.25%; Collagen—0.375%–0.625%; Lanolin—0.075%–0.125%; Methylchloroisothia-zolinone—0.0375%–0.0625%; Methylisothia-zolinone—0.0375%–0.0625%; Citric Acid—0.01875%–0.03125%.

116. The shampoo product of claim 115, consisting essentially of said ingredients and water.

117. The shampoo product of claim 115, consisting of said ingredients and water.

118. A method of cleaning/maintaining hair comprising using the shampoo product of claim 107.

119. The method of claim 118, wherein the shampoo product consists essentially of said ingredients and water.

120. The method of claim 118, wherein the shampoo product consists of said ingredients and water.

121. The method of claim 118, wherein said ingredients are present in the following amounts:

Poliquaternium-11—3.5%–10.5%; Dimethicone Copolyol—0.5%–1.5%; Zinc Oxide—0.5%–1.5%; Boric Acid—0.5%–1.5%; Collagen—0.25%–0.75%; Lanolin—0.05%–0.15%; Methylchloroisothia-zolinone—0.025%–0.075%; Methylisothia-zolinone—0.025%–0.075%; Citric Acid—0.0125%–0.0375%.

122. The method of claim 121, wherein the shampoo product consists essentially of said ingredients and water.

123. The method of claim 121, wherein the shampoo product consists of said ingredients and water.

124. The method of claim 118, wherein said ingredients are present in the following amounts:

Poliquaternium-11—5.25%–8.75%; Dimethicone Copolyol—0.75%–1.25%; Zinc Oxide—0.75%–1.25%; Boric Acid—0.75%–1.25%; Collagen—0.375%–0.625%; Lanolin—0.075%–0.125%; Methylchloroisothia-zolinone—0.0375%–0.0625%; Methylisothia-zolinone—0.0375%–0.0625%; Citric Acid—0.01875%–0.03125%.

125. The method of claim 124, wherein the shampoo product consists essentially of said ingredients and water.

126. The method of claim 124, wherein the shampoo product consists of said ingredients and water.

127. A shampoo product comprising the following ingredients in the following amounts and water:

2.5%–50.0% by weight Alcohol; 0.27%–5.4% by weight Zinc Oxide; 0.23%–4.6% by weight Boric Acid; 0.2%–4.0% by weight Pathenol; 0.10%–4.0% by weight Hydrolyzed Serum Protein; 0.10%–4.0% by weight Yeast Extract; 0.10%–4.0% by weight Glucose; 0.10%–4.0% by weight Niacinamide; 0.10%–4.0% by weight Pyridoxine; 0.10%–4.0% by weight Hydrolized Glycosaminoglycans; 0.10%–4.0% by weight Biotin; 0.03%–0.60% by weight Fragrance; 0.01%–0.20% by weight Polysorbate 20; 0.01%–0.20% by weight Arnica Montana Extract; 0.005%–0.10% by weight Methylchloroisothia-zolinone; 0.005%–0.10% by weight Methylisothia-zolinone.

128. The shampoo product of claim 127, consisting essentially of said ingredients and water.

129. The shampoo product of claim 127, consisting of said ingredients and water.

130. The shampoo product of claim 127, wherein said ingredients are present in the following amounts:

Alcohol—12.5%–37.5%; Zinc Oxide—1.35%–4.05%; Boric Acid—1.15%–3.45%; Pathenol—1.0%–3.0%; Hydrolyzed Serum Protein—0.50%–1.5%; Yeast Extract—0.50%–1.5%; Glucose—0.50%–1.5%; Niacinamide—0.50%–1.5%; Pyridoxine—0.50%–1.5%; Hydrolized Glycosaminoglycans—0.50%–1.5%; Biotin—0.50%–1.5%; Fragrance—0.15%–0.45%; Polysorbate 20—0.05%–0.15%; Arnica Montana Extract—0.05%–0.15%; Methylchloroisothia-zolinone—0.025%–0.075%; Methylisothia-zolinone—0.025%–0.075%.

131. The shampoo product of claim 130, consisting essentially of said ingredients and water.

132. The shampoo product of claim 130, consisting of said ingredients and water.

133. The shampoo product of claim 127, wherein said ingredients are present in the following amounts:

Alcohol—18.75%–31.25%; Zinc Oxide—2.025%–3.375%; Boric Acid—1.725%–2.875%; Pathenol—1.5%–2.5%; Hydrolyzed Serum Protein—0.75%–1.25%; Yeast Extract—0.75%–1.25%; Glucose—0.75%–1.25%; Niacinamide—0.75%–1.25%; Pyridoxine—0.75%–1.25%; Hydrolized Glycosaminoglycans—0.75%–1.25%;

Biotin—0.75%–1.25%; Fragrance—0.225%–0.375%; Polysorbate 20—0.075%–0.125%; Arnica Montana Extract—0.075%–0.125%; Methylchloroisothiazolinone—0.0375%–0.0625%; Methylisothiazolinone—0.0375%–0.0625%.

134. The shampoo product of claim 133, consisting essentially of said ingredients and water.

135. The shampoo product of claim 133, consisting of said ingredients and water.

136. A method of cleaning/maintaining hair comprising using the shampoo product of claim 127.

137. The method of claim 136, wherein the shampoo product consists essentially of said ingredients and water.

138. The method of claim 136, wherein the shampoo product consists of said ingredients and water.

139. The method of claim 136, wherein said ingredients are present in the following amounts:

Alcohol—12.5%–37.5%; Zinc Oxide—1.35%–4.05%; Boric Acid—1.15%–3.45%; Pathenol—1.0%–3.0%; Hydrolyzed Serum Protein—0.50%–1.5%; Yeast Extract—0.50%–1.5%; Glucose—0.50%–1.5%; Niacinamide—0.50%–1.5%; Pyridoxine—0.50%–1.5%; Hydrolized Glycosaminoglycans—0.50%–1.5%; Biotin—0.50%–1.5%; Fragrance—0.15%–0.45%; Polysorbate 20—0.05%–0.15%; Arnica Montana Extract—0.05%–0.15%; Methylchloroisothia-zolinone—0.025%–0.075%; Methylisothia-zolinone—0.025%–0.075%.

140. The method of claim 139, wherein the shampoo product consists essentially of said ingredients and water.

141. The method of claim 139, wherein the shampoo product consists of said ingredients and water.

142. The method of claim 136, wherein said ingredients are present in the following amounts:

Alcohol—18.75%–31.25%; Zinc Oxide—2.025%–3.375%; Boric Acid—1.725%–2.875%; Pathenol—1.5%–2.5%; Hydrolyzed Serum Protein—0.75%–1.25%; Yeast Extract—0.75%–1.25%; Glucose—0.75%–1.25%; Niacinamide—0.75%–1.25%; Pyridoxine—0.75%–1.25%; Hydrolized Glycosaminoglycans—0.75%–1.25%; Biotin—0.75%–1.25%; Fragrance—0.225%–0.375%; Polysorbate 20—0.075%–0.125%; Arnica Montana Extract—0.075%–0.125%; Methylchloroisothiazolinone—0.0375%–0.0625%; Methylisothiazolinone—0.0375%–0.0625%.

143. The method of claim 142, wherein the shampoo product consists essentially of said ingredients and water.

144. The method of claim 142, wherein the shampoo product consists of said ingredients and water.

* * * * *